United States Patent
Nozaki (10) Patent No.: US 8,349,536 B2
(45) Date of Patent: Jan. 8, 2013

(54) DITHIANE DERIVATIVE, POLYMER, RESIST COMPOSITION, AND METHOD FOR MANUFACTURING SEMICONDUCTOR DEVICE USING SUCH RESIST COMPOSITION

(75) Inventor: Koji Nozaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 155 days.

(21) Appl. No.: 12/955,462

(22) Filed: Nov. 29, 2010

(65) Prior Publication Data

US 2011/0076620 A1    Mar. 31, 2011

Related U.S. Application Data

(63) Continuation of application No. PCT/JP2008/059921, filed on May 29, 2008.

(51) Int. Cl.
G03F 7/004     (2006.01)
G03F 7/00      (2006.01)
C08F 220/38    (2006.01)

(52) U.S. Cl. ............. 430/270.1; 526/286; 526/319; 430/311

(58) Field of Classification Search ......... 526/256, 526/318, 286, 329.7, 245; 549/20
See application file for complete search history.

(56) References Cited

U.S. PATENT DOCUMENTS

| 5,356,979 | A |   | 10/1994 | Tai et al. |
| 5,550,202 | A |   | 8/1996  | Tai et al. |
| 6,307,062 | B1 | * | 10/2001 | Caye et al. ............... 549/11 |
| 2002/0049289 | A1 |   | 4/2002 | Caye et al. |
| 2006/0246373 | A1 |   | 11/2006 | Wang |

FOREIGN PATENT DOCUMENTS

| JP | 6-073130 A | 3/1994 |
| JP | 2804840 B2 | 9/1998 |
| JP | 2000-509075 A | 7/2000 |
| JP | 2002-030082 A | 1/2002 |
| JP | 3284730 B2 | 5/2002 |
| JP | 2002-255930 A | 9/2002 |
| JP | 2003-128668 A | 5/2003 |
| JP | 2004-162040 A | 6/2004 |
| JP | 2005-133071 A | 5/2005 |
| JP | 2006-089412 A | 4/2006 |
| JP | 2006-309245 A | 11/2006 |
| JP | 2007-91652 A | 4/2007 |
| WO | 2009/078078 A1 | 6/2009 |

OTHER PUBLICATIONS

Caye, F. et al. "A convenient high yield synthesis of functional methacrylates via dethioacetalization. Synthesis of methacrylate S,S-acetal derivatives as intermediates," Phosphorus Sulfur Silicon Relat. Elem., 143, 1998, pp. 197-220.

Blakey, I. et al. "Novel High-Index Resists for 193 nm Immersion Lithography and Beyond," Proc. of SPIE, vol. 6519, 2007, pp. 651909-1-651909-9.

International Search Report of PCT/JP2008/059921, mailing date Jun. 24, 2008.

* cited by examiner

*Primary Examiner* — Cynthia Kelly
*Assistant Examiner* — Alyssa L Cepluch
(74) *Attorney, Agent, or Firm* — Westerman, Hattori, Daniels & Adrian, LLP (57) ABSTRACT

A dithiane derivative, having a structure expressed by the following general formula 1:

General Formula 1

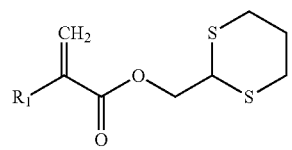

where $R_1$ is —H, or —$CH_3$, a polymer containing a monomer unit containing the dithiane derivative, a resist composition containing the polymer, and a method for manufacturing a semiconductor device using the resist composition.

13 Claims, 3 Drawing Sheets

DITHIANE DERIVATIVE, POLYMER, RESIST COMPOSITION, AND METHOD FOR MANUFACTURING SEMICONDUCTOR DEVICE USING SUCH RESIST COMPOSITION

CROSS-REFERENCE TO RELATED APPLICATIONS

This application is a continuation of PCT/JP2008/059921, filed on May 29, 2008, the entire contents of which are incorporated herein by reference.

FIELD

The present invention relates to a novel dithiane derivative, polymer containing the dithiane as a monomer unit, a resist composition containing such the polymer, and a method for manufacturing a semiconductor device using such the resist composition.

BACKGROUND

In the current technology of the semiconductor integrated circuit, higher integration has been achieved and as a result, the minimum pattern size reaches the region of 100 nm or smaller. For the formation of fine patterns, exposure technique is regarded as very important, and the exposure technique enables to attain a desired pattern in the following manner. At first, a resist film is applied onto a substrate to be processed (surface to be processed) to which a thin film has been formed, the resist film is selectively exposed with light and then developed so as to form a pattern, a dry etching is performed using the thus obtained pattern as a mask, and finally the resist pattern is removed to obtain the desired pattern.

In order to realize downsizing of the pattern, it is effective to improve and develop both an exposure light source using the shorten wavelength and a resist material of high resolution corresponding to the characteristics of the exposure light source. Currently, ArF excimer laser exposure tools have been shipping on the market. However, these exposure tools themselves are quite expensive and a large scale of cost is expected at the time the exposure tool is updated for the purpose of shortening the wavelength of the exposure tool. Moreover, it is not easy to develop a resist material which corresponds to the shorten wavelength of exposure light, and it is extremely difficult to realize the downsizing of the pattern by only shortening the wavelength of the exposure device.

For these reasons, much attention has been attracted to a new exposure technique, a liquid immersion lithography, in the art. In this method, the space between the projection lens and wafer in the exposure device is filled with liquid having a lager refractive index n than that of air so as to improve and obtain higher resolution than that of the related art.

The resolution of the exposure device is determined by using the following Calculation Formula 1:

Resolution $R$=Coefficient $k$×Wavelength $\lambda$ of light source/Numerical aperture NA    Calculation Formula 1

As represented with Calculation Formula 1, the resolution R improves (be smaller), as the wavelength $\lambda$ of an exposure light source is shorter and the numerical aperture NA is larger. Note that, the numerical aperture of the projection lens is represented as: NA=n×sin $\alpha$, where n is refractive index of a medium through which the exposure light is transmitted, and $\alpha$ is an angle formed between the exposure light and a light axis of the projection lens. Since the exposure of light is generally performed in atmospheric air, the refractive index n is 1 (i.e., n=1). The liquid immersion exposure method applies the exposure system in which the space between the projection lens and the wafer is filled with a liquid having the refractive index n larger than 1 (i.e., n>1). Accordingly, the refractive index is enlarged from 1 to n (a number larger than 1) in the relative formula of the numerical aperture NA: NA=n×sin $\alpha$. At the incident angle $\alpha$ of the same exposure light, the resolution R (minimum resolution size) will be reduced in 1/n as NA is enlarged n time(s). In addition, there is also the advantage such that, in the case where the value of NA is set the same, the depth of focus is deepened n times as $\alpha$ can be reduced by enlarging n.

In accordance with the conventional exposure in the air, the numerical aperture NA cannot be adjusted to 1 or larger, as a refractive index of the air between the resist and the lens becomes the factor to limit the numerical aperture NA. However, in accordance with liquid immersion lithography using water, the refractive index relative to the light having a wavelength of 193 nm is increased to 1.44. Therefore, it has been said that the numerical aperture NA can be increased up to about 1.4 on theory. However, as the numerical aperture NA is increased, the angle of the light incident to the resist film is significantly increased. Therefore, the depth of focus (a margin of the focal distance capable of resolution) is reduced. Moreover, to attain higher resolution (the smaller value of the resolution R), liquid immersion lithography of the next generation, which uses a medium having the higher refractive index (n>1.6) than that of water, has been studied. In the case of this liquid immersion lithography of the next generation, it is theoretically possible to increase the numerical aperture NA by about 1.6 times for the exposure in the air, but the current material for an ArF resist has the insufficient refractive index (the refractive index n is about 1.7 to the light having a wavelength of 193 nm). Therefore, the total reflection occurs on the surface of the resist film so that the light does not reach to the inner part of the resist film. As a result, an image cannot be formed, and hence a pattern cannot be formed.

To solve these problems, the studies have been conducted to increase a refractive index of a resist material. However, not so many materials, which can effectively increase a refractive index with maintaining transparency at 193 nm, without impairing acid reactivity desirable for forming a pattern, have not been known in the art. As a familiar example of the material whose refractive index is increased, a resin lens used for glasses and the like has been known. For such material, it is common that the refractive index of the material is increased by introducing heavy metals, aromatic rings, heavy halogen atoms such as bromine and iodine, or sulfur atoms into the material. In the case of the ArF resist material, however, there is a limitation in the method for introducing sulfur atoms because of the transparency at 193 nm, or the problem of contamination.

As prior examples of the resist material whose refractive index is increased, those using a resin containing sulfur, which has a problem in the transparency thereof, disclosed in Idriss Blakey et al., *Proc. SPIE*, 6519, 651909 (2007), an alicyclic material disclosed in Japanese Patent Application Laid-Open (JP-A) No. 2006-89412, and a curable composition containing aromatic heterocyclic (meth)acrylate disclosed in JP-A No. 2005-133071 have been known. Therefore, it has been desired to develop a material whose refractive index is increased, and which can be easily produced.

SUMMARY

According to an aspect of the invention, a dithiane derivative has a structure expressed by the following general formula 1:

General Formula 1 where $R_1$ is —H, or —CH$_3$.

According to another aspect of the invention, a polymer contains a monomer unit containing the dithiane derivative.

According to another aspect of the invention, a resist composition contains the polymer.

According to another aspect of the invention, the method for manufacturing a semiconductor device contains: forming a resist film formed of the resist composition on a processing surface; exposing the resist film to light; and developing the resist film so as to pattern the resist film.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS (Dithiane Derivative)

The dithiane derivative contains a structure expressed by the following general formula 1:

General Formula 1

In the general formula 1, $R_1$ is —H, or —CH$_3$. As $R_1$, a trifluoromethyl group is also preferable. In addition, a thioester structure is suitable for increasing a refractive index. Furthermore, those derivatives including dithiane whose sulfur atom(s) is oxidized to be sulfone(s) are preferable for increasing a transparency of the resulting resist composition containing such derivative as a monomer unit of a polymer contained therein, relative to light of a short wavelength range.

Since sulfur elements are contained in the dithiane derivative, when a polymer containing this dithiane derivative as a monomer unit (a constitutional unit) is used in a resist composition, a refractive index of the resin for the resist composition is increased without impairing the properties of the resist composition, such as transparency and acid sensitivity, and the resist composition can be applicable to the liquid immersion lithography of the next generation, which attempts to form a down-sized pattern using a lens of a large aperture (a lens having a large numerical aperture, NA).

Examples of the dithiane derivative include the compounds expressed by the following general formulae:

-continued

Note that, in the formulae above, $R_x$ is H or an alkyl group.

<Production Method of Dithiane Derivative>

These dithiane derivatives can be synthesized in accordance with the conventional methods, and as described in Idriss Blakey et al., *Proc. SPIE*, 6519, 651909 (2007), the dithiane derivative can be generally obtained by an esterification reaction between acid chloride and an alcohol compound or a thiol compound. Specifically, for example, the dithiane derivative can be easily obtained in the following manner. First, the same molar amounts of an alcohol or thiol compound and a base catalyst such as triethyl amine are added to a solvent such as dried methylene chloride, and the mixture is cooled to 0° C. to −20° C. Thereafter, for example, acryloyl chloride is added dropwise thereto through a dropping funnel, triethyl amine salt is removed after consumption of the raw material is confirmed by a thin film chromatography or gas chromatography, and then purification is performed for example, by column chromatography to easily afford a desired compound.

(Polymer)

Next, the polymer (the resin for a positive resist composition) containing the dithiane derivative as a monomer unit will be explained.

The polymer is suitably selected depending on the intended purpose without any restriction, provided that it contains the dithiane derivative as a monomer unit. For example, the polymer may be a homopolymer of the dithiane derivative, or copolymer obtained by copolymerizing the dithiane derivative with other monomer units.

Since the polymer contains the monomer unit containing the dithiane derivative, when a polymer containing this dithiane derivative as a monomer unit is used in a resist composition, a refractive index of the resin for the resist composition is increased without impairing the properties of the resist composition, such as transparency and acid sensitivity, and the resist composition can be applicable to the liquid immersion lithography of the next generation, which attempts to form a down-sized pattern using a lens of a large aperture (a lens having a large numerical aperture, NA).

<Amount of Dithiane Derivative in Polymer>

It is desirable that the amount of the dithiane derivative in the polymer (the resin for a positive resist composition) be determined carefully considering the predetermined refractive index, resulting properties of a resist composition, such as sensitivity, resolution and etching resistance. The amount of the monomer unit containing the dithiane derivative is preferably in the range of 0.1 mol % to 70 mol %, more preferably 10 mol % to 50 mol %. When the amount of the dithiane derivative in the polymer is less than 0.1 mol %, the refractive index of the resulting resin for a resist composition cannot be increased. When the amount of the dithiane derivative in the polymer is more than 70 mol %, an effect originated from other monomer units to be copolymerized (for example, high optical transparency and high etching resistance originated from an adamanthyl group, or high adhesion originated from a lactone group) cannot be attained, and absorption of ultraviolet rays is increased, which reduces the transmittance of the light having a wavelength of 193 nm.

<Other Monomer Units>

Other monomer units can be suitably selected depending on the intended purpose without any restriction, but those monomer units having acid labile groups (acid labile sites) (e.g. monomer units having alicyclic groups that react with acid) are preferable. The resin for used in a positive resist composition itself is generally alkali-insoluble, but the resin becomes alkali-soluble after the acid labile groups are reacted.

<<Acid Reactive Group>>

The acid labile group is suitably selected depending on the intended purpose without any restriction. Various acid labile group used in the art can be used here. Preferably examples thereof include: tertiary ester such as t-butyl group; acetal group such as ethoxyethyl; condensed hydrocarbon group such as 2-oxocyclohexyl group, 2-alkyl-2-adamanthyl group, 1-alkyl-1-cyclopenthyl group, 1-alkyl-1-cyclohexyl group, 2-adamanthyloxymethyl group, and 1-methyladamanthyloxymethyl group. Among them, the acid labile group having a condensed hydrocarbon group such as 2-alkyl-2-adamanthyl group, 2-adamanthyloxymethyl group, or 1-methyl adamanthyloxymethyl group is more preferable since such acid labile group provides etching resistance required for a resist and transparency at the wavelength of 193 nm.

Moreover, the polymer containing the dithiane derivative as a monomer unit preferably further contains a monomer unit including a lactone derivative (e.g., a monomer unit containing a lactone group that will be a side chain in a polymer) in addition to the monomer unit having the acid labile group mentioned above. Since a lactone ring is highly polar, it contributes to adhesion properties of a resist pattern, and it also imparts a suitable alkali-solubility at the exposed area due to slight alkali-solubility thereof.

<<Lactone Derivative>>

A lactone derivative is suitably selected depending on the intended purpose without any restriction. Preferable examples thereof include γ-butyrolactone group, δ-lactone group, alicyclic lactone combined with norbornane or cyclohexane ring. Among them, the alicyclic lactone is particularly preferable since it contributes to an etching resistance of the resulting resist composition.

In the case where the polymer (the resin) contains the monomer unit containing the dithiane derivative and acid labile group, and the monomer unit containing a lactone derivative, the ratio of these units is arbitral, but it is desirable that the ratio is adjusted considering the balance between obtainable resolution, etching resistance and refractive index.

Moreover, the polymer (the resin for a positive resist composition) containing the monomer unit containing the dithiane derivative may further contain a monomer unit having other functions than mentioned above. Examples of such unit include a unit containing an alkali-soluble group (e.g. carboxyl group and hexafluorocarbinol group) at a site which will be a side chain in the resulting polymer, a unit containing a hydroxyl group such as 2-hydroxyethyl group or 3-hydroxyadamanthyl group, and the like. The amounts of these units in the polymer should be carefully determined considering desired properties such as adhesion of the resist film to a substrate, alkali-dissolution rate of the exposed area, and the like.

(Resist Composition)

The resist composition is suitably selected depending on the intended purpose without any restriction, provided that it contains the aforementioned polymer. In the case of the positive resist composition, the resist composition contains an acid-generating agent together with the polymer (the resin). Moreover, the resist composition may contain the dithiane derivative itself as an additive.

<Acid Generating Agent>

The acid-generating agent is suitably selected from those known in the art without any restriction. Preferable examples thereof include commonly used trifluoromethanesulfonium salt, perfluorobutanesulfonium salt, and perfluorodisulfone-imide salt. The amount thereof in the resist composition is preferably in the approximate range of 0.1 parts by mass to 10 parts by mass relative to 100 parts by mass of the resin, though it is adjusted depending on the balance with the desirable sensitivity or resolution to be obtained.

<Solvent>

A solvent used for the positive resist composition is suitably selected without any restriction, provided that it is commonly used for resist compositions, but is preferably selected considering solubility and coating performance of the polymer (the resin), the acid-generating agent, and other additives.

The solvent is suitably selected depending on the intended purpose without any restriction. Preferable examples of such solvent include propylene glycol monomethylether acetate, 2-heptanone, ethyl lactate, and cyclohexanone. Optionally, an auxiliary solvent can also be used. As an auxiliary solvent, propylene glycol monomethyl ether or γ-butyrolactone is preferably used. An organic solvent having a boiling point of about 100° C. to about 200° C. and excellent solubility of the resin is especially preferably used. Use of such the organic solvent is preferable, since it is suitably used for coating, and the rapid drying is prevented during the coating process.

<Quencher>

Moreover, the resist composition may further contain a quencher. By adding a quencher to the resist composition, the exposure contrast can be improved. The quencher is suitably selected depending on the intended purpose without any restriction. Preferable examples thereof include nitrogen-containing compounds such as tri-n-octyl amine, 2-methylimidazole, 1,8-diazabicyclo[5.4.0]undec-7-ene (DBU), 1,5-diazabicyclo[4.3.0]non-5-ene (DBN), diphenyl amine, and triethanol amine.

<Surfactant>

The resist composition may further contain a surfactant. A surfactant is added to the resist composition mainly for improving the coating performance thereof. The surfactant is suitably selected depending on the intended purpose without any restriction. Preferable examples thereof include nonionic surfactants free from a metal ion (e.g. sodium salt, and potassium salt). Particularly preferable examples thereof include surfactants based of polyoxyethylene-polyoxypropylene condensate and derivatives thereof, polyoxyalkylene alkyl ether-based surfactants, polyoxyethylene alkyl ether-based surfactants, polyoxyethylene derivative-based surfactants, sorbitane fatty acid ester-based surfactants, glycerin fatty acid ester-based surfactants, primary alcohol ethoxylate-based surfactants, phenol ethoxylate-based surfactants, silicone-based surfactants, and fluorosurfactants. Moreover, the surfactant may be selected from ionic surfactants other than the ones mentioned above, provided that the ionic surfactants are of metal salt-free. It is assumed that the same effect can be attained even if the aforementioned nonionic surfactant is replaced with such the metal salt-free ionic surfactant.

Since the resist composition contains the polymer, a refractive index of the resist base resin is increased without impairing the properties of the resist composition, such as transparency and acid sensitivity, and the resist composition can be applicable to the liquid immersion lithography of the next generation, which attempts to form a down-sized pattern using a lens of a large aperture (a lens having a large numerical aperture NA).

(Method for Manufacturing Semiconductor Device)

The method for manufacturing a semiconductor device contains at least a resist film forming step, an exposing step, and a developing step, preferably further contains a heating step, and may further contain suitably selected other steps, if necessary. It is preferred that the heating step be performed after the exposing step.

In the method mentioned above, a resist film containing the resist composition is formed on a processing surface, exposure light is selectively applied to the resist film, and then resist film is developed to form a pattern in the resist film.

<Resist Film Forming Step>

The resist film forming step is forming a resist film formed of the resist composition on a processing surface.

The resist film can be formed by a method known in the art, such as by coating. The coating method is suitably selected from the conventional coating methods depending on the intended purpose without any restriction. Preferable examples thereof include spin coating. In the case of the spin coating, as preferred conditions thereof, the rotation number is about 100 rpm to about 10,000 rpm, preferably 800 rpm to 5,000 rpm, and the duration is about 1 second to about 10 minutes, preferably 1 second to 90 seconds.

The thickness of the coating is suitably selected depending on the intended purpose without any restriction.

It is preferred that the coated resist composition be pre-baked (heated and dried) during or after coating. The conditions and method of the pre-baking are suitably selected depending on the intended purpose without any restriction, provided that the pre-backing will not soften the resist film. For example, the temperature of the pre-baking is preferably about 40° C. to about 150° C., more preferably 80° C. to 120° C., and the duration thereof is preferably about 10 seconds to about 5 minutes, more preferably 30 seconds to 90 seconds.

The processing surface is suitably selected depending on the intended purpose without any restriction. In the case where the resist film is formed in an electronic device such as a semiconductor, examples of the processing surface include surface layers of various members of the semiconductor device, preferably a substrate such as a silicon wafer and a surface thereof, and a low dielectric film such as various oxide films and a surface thereof.

The low dielectric film is suitably selected depending on the intended purpose without any restriction, but is preferably a film having a dielectric constant of 2.7 or less. Preferable examples of such low dielectric film include a porous silica film, and a fluororesin film.

The porous silica film can be formed, for example, by applying a material for forming a silica film, subjecting the applied material to a heat treatment so as to remove a solvent contained in the material, and baking the applied material.

In the case where the fluororesin film is a fluorocarbon film, the fluororesin film can be formed, for example, by deposition in accordance with a RFCVD method (power: 400 W) using a mixed gas of $C_4F_8$ and $C_2H_2$ or $C_4F_8$ gas as a source.

<Exposing Step>

The exposing step is selectively exposing the resist film to light.

The exposure can be suitably performed by means of any exposure device known in the art, and is carried out by applying light to the resist film. As a result of the application of the light, the photo acid-generating agent contained in the exposed area of the resist composition is decomposed to generate an acid, which initiates a curing reaction of the resist composition to form a latent pattern.

The light is applied to a partial area of the resist film. The polarity of the resist film is increased as a result of that side chains of the resin are detached by the acid reaction in the partial area due to the application of the light, so that the highly polarized partial area is removed in the developing step described later to form a resist pattern.

In the exposing step, the application of light is carried out in accordance with liquid immersion lithography. Here, a medium for use in the liquid immersion lithography may be water, but is preferably liquid having a higher refractive index than that of water relative to light having a wavelength of 193 nm.

The exposure light is suitably selected depending on the intended purpose without any restriction. Preferably examples thereof include activation energy radiation such as ultraviolet ray, X-ray, electron ray, excimer laser beam, EUV light, and focused ion beam.

In the case where the ultraviolet ray is used, the ultraviolet ray having a wavelength of 200 nm or shorter is more preferable.

In the case where the excimer laser beam is used, KrF excimer laser light (wavelength of 248 nm), ArF excimer laser light (wavelength of 193 nm), $F_2$ excimer laser light (wavelength of 157 nm), or the like is preferable.

<Heating Step>

The heating step is subjecting the exposed resist film to a heating treatment (a post-exposure bake, PEB).

As a result of the heating, the elimination reaction of the side chain of the resist resin in the exposed area is accelerated.

The heating temperature is preferably 50° C. to 200° C., more preferably 70° C. to 180° C. When the temperature is lower than 50° C., the elimination reaction of the side chain of the resin may not be progressed. When the temperature is higher than 200° C., the resist composition, which forms the resist film, may be thermally decomposed.

<Development Step>

The development step is removing the exposed area of the resist film to develop the resist film, after exposing the resist film in the exposing step and reacting the exposed area of the resist film, so as to form a pattern of the resist film (a resist pattern).

The method for removing the reacted area is suitably selected depending on the intended purpose without any restriction, and examples thereof include a method for removing the reacted area using a developer.

The developer is suitably selected depending on the intended purpose without any restriction, and is preferably an alkali solution. Specific examples of the alkali solution include a tetramethylammoniumhydroxide (TMAH) solution, and a choline solution, which are commonly used in the production of a semiconductor device.

As a result of the developing, the area of the resist film where the light is applied is dissolved and removed to form (develop) a resist pattern.

<Other Steps>

Other steps are suitably selected depending on the intended purpose without any restriction. Examples thereof include a pattern transferring step.

<<Pattern Transferring Step>>

The pattern transferring step is etching the processing surface using the pattern of the resist film (the resist pattern) as a mask so as to pattern the processing surface.

The method for the etching is suitably selected from the methods known in the art depending on the intended purpose without any restriction. Preferable examples thereof include dry etching. The conditions of the etching are suitably selected depending on the intended purpose without any restriction.

The method for manufacturing a semiconductor device is suitable for the formation of various resist patterns, such as a line-space pattern, a hole pattern (for a contact hole), a pillar pattern, a trench pattern, and a line pattern, and the resist pattern formed by the method for manufacturing a semiconductor can be used, for example, as a mask pattern, and a reticle pattern, and are suitably used for the production of functional parts such as metal plugs, various wirings, magnetic heads, liquid crystal displays (LCD), plasma display panels (PDP), and a surface acoustic wave (SAW) filter, optical parts used for connection of optical wirings, minute parts such as microactuator, and a semiconductor device.

Specifically, by selectively depositing or etching using as a mask pattern, the resist pattern formed by the method for manufacturing a semiconductor device, a device having a fine processing pattern having a constant line width and formed of a metal or other materials can be manufactured, and for example, a semiconductor device having a fine wiring having a line width of 100 nm or smaller can be manufactured.

Moreover, in accordance with the method for manufacturing a semiconductor device, a fine and precise resist pattern can be accurately formed without causing the defects in the shape, and a higher performance semiconductor device having a fine wiring pattern, such as a flash memory, DRAM, and FRAM, can be efficiently mass-produced by using the resist pattern.

In accordance with the invention, various problems in the art can be solved, and there are provided a dithiane derivative useful for increasing a refractive index of a resin for a resist composition without impairing properties of the resist composition such as transparency and acid sensitivity, a polymer containing a monomer unit containing the dithiane derivative, a resist composition containing the polymer, and a method for manufacturing a semiconductor device using the resist composition.

EXAMPLES

Examples of the invention will be explained hereinafter, but these examples are merely some of examples of the invention, and these examples shall not be construed as to limit the mixing ratios of the compositions, or the scope of the invention. Note that, the determination and evaluation of compounds were performed by means of NMR (JNM-GX500, manufactured by JEOL Ltd.), FTIR (IRPrestige-21, manufactured by Shimadzu Corporation), UV (U-3900H, manufactured by Hitachi, Ltd.), GPC (HLC-8220, manufactured by Tosoh Corporation).

Synthesis Example 1

Synthesis of 1,3-dithianylmethyl methacrylate

Dithiane Derivative of the Following Formula 2

To a 100-mL three-necked flask, 3.41 g of 2-hydroxymethyl-1,3-dithiane, which had been synthesized in accordance with the method known in the art (see Tetrahedron Letters, 41, 5653-5657 (2000)) using 2-carboethoxy-1,3-dithiane as a starting material, and 2.3 g of triethyl amine were added, and to this mixture 40 mL of dried methylene chloride were added and the resulting mixture was stirred with a stirrer bar coated with Teflon™ at 0° C. under nitrogen atmosphere. To the mixture, 2.3 g of methacryloyl chloride was slowly added through a dropping funnel, and the resulting mixture was reacted at 0° C. for 2 hours, and the temperature of the mixture was allowed to return to room temperature, followed by reacting for another 2 hours. After confirming consumption of the starting material by a thin layer chromatography (TLC), the reaction solution was poured into a 300-mL separatory funnel, washed with 100 mL of water, followed with 100 mL of saturated NaCl solution (brine), and dried with anhydrous sodium sulfate. From the obtained solution, the solvent was removed by an evaporator, to obtain an oily crude product. The crude product was purified by silica gel chromatography using a mixed solution of n-hexane and ethyl acetate to yield 3.64 g of 1,3-dithianylmethyl methacrylate (a dithiane derivative of the following formula 2) (yield: 79.4%).

(1) $^1$H-NMR (500 MHz, CDCl$_3$, internal standard TMS, δ in ppm): 1.98 (s, 3H), 1.95-2.1 (m, 2H), 2.73-2.78 (m, 2H), 2.95 (br, 2H), 4.17 (t, 1H), 4.47 (d, 2H), 5.61 (s, 1H), 6.17 (m, 1H)

(2) IR (KBr, cm$^{-1}$): 2949, 2899, 1719, 1636, 1452, 1422, 1319, 1294, 1152, 943

(3) Refractive index nD=1.547

Formula 2

Synthesis Example 2

Synthesis of poly(2-methyl-2-adamanthyl-methacrylate-1,3-dithianylmethyl methacrylate)

Dithiane Derivative of the Following Formula 3

To a 50-mL eggplant-shaped flask, 1.12 g of 2-methyl-2-adamanthyl methacrylate and 1.0 g of 1,3-dithianylmethyl methacrylate were added. To this, 6.1 mL of dioxane was added, and the mixture was stirred with a stirrer bar coated with Teflon™, and nitrogen gas was bubbled therein for 15 minutes to sufficiently remove oxygen from the reaction atmosphere. To this, 0.23 g of AIBN was added as a radical polymerization initiator, and the flask was placed in an oil bath at 70° C. for 5 hours. The obtained reaction mixture was cooled to room temperature, and diluted with dioxane to be about 25 mL in volume. The solution was dropped into 500 mL of methanol with stirring to give white precipitate. After filtering with a glass filter, the obtained precipitated resin was dried in vacuo at 50° C. for 6 hours. The resulted resin was dissolved in about 20 mL of THF, was again precipitated in 500 mL of methanol, and filtered and dried in the aforementioned manner to provide a final polymer (a polymer of the following formula 3). The yield was 1.5 g, the weight average molecular weight was 25,100 (standard polystyrene equivalent), and polydispersion (Mw/Mn) was 2.49. Note that, the composition ratio was determined by $^1$H-NMR (JNM-GX500, manufactured by JEOL Ltd.) and the molecular weight was measured by GPC (HLC-8220 GPC, manufactured by Tosoh Corporation).

IR (KBr disk, cm$^{-1}$): 2990, 1724, 1258, 1148, 1103

Formula 3

Example 1 and Comparative Example 1

-Measurement of Refractive Index-

A resin solution was prepared using each of the resin of Synthesis Example 2 expressed by the formula 3 (Example 1), and a commonly available resin for an ArF resist composition, expressed by the following formula 4 (Comparative Example 1). Specifically, 750 parts by mass of 2-heptanone and 250 parts by mass of γ-butyl lactone were added to 100 parts by mass of the resin to prepare the resin solution. The obtained solution was filtered through a 0.2 μm Teflon™ membrane filter to remove particles and the like. The resulting solution was spin-coated on a silicon wafer, and baked at 110° C. for 60 seconds to form a resin film. The refractive index of each resin film was measured by a spectral ellipsometer (GES-5, manufactured by SOPRALAB). The results are presented in Table 1.

Formula 4

TABLE 1

| Resin | Refractive index (400-850 nm) |
|---|---|---|
| Example 1 | Formula 3 | 1.533 |
| Comparative Example 1 | Formula 4 | 1.504 |

As seen from Table 1, a larger refractive index can be attained when the polymer (the resin) containing the dithiane derivative as a monomer unit is used (Example 1), compared to the case when the conventional resin for an ArF resist composition is used (Comparative Example 1).

Example 2

-Preparation of Resist Composition-

A resist composition for liquid immersion lithography was prepared in the accordance with the following formulation, using the polymer (the resin) expressed by Formula 3. As an acid-generating agent, triphenylsulfonium nonafluorobutane sulfonate (manufactured by Midori Kagaku Co., Ltd.) was used, and as a resist solvent, 2-heptanone and γ-butyl lactone were used.

| Resin | 100 parts by mass |
|---|---|
| Acid-generating agent | 3 parts by mass |
| Tri-n-octyl amine | 0.02 parts by mass |
| 2-heptanone | 1,000 parts by mass |
| γ-butyl lactone | 300 parts by mass |

Example 3

-Evaluation on Resist Performance-

Onto a substrate to which an undercoat antireflection film (BARC, ARC-39, manufactured by Nissan Chemical Industries, Ltd.) had been coated, the resist composition prepared in Example 2 was spin-coated, and baked at 110° C. for 60 seconds to form a resist film having a thickness of 200 nm. The resist film was then subjected to exposure in accordance with ArF liquid immersion lithography, baked at 130° C. for 60 seconds, developed with a 2.38% TMAH solution for 60 seconds, and rinsed with pure water, to obtain a line and space pattern (i.e. a L/S pattern) of 200 nm. Note that, the optical transmittance of the resist film was 40% with respect to light having a wavelength of 193 nm, and thus the resist film had the transparency necessary for the patterning.

TABLE 2

|  | Sensitivity (mJ/cm$^2$) | Residual |
|---|---|---|
| Example 3 | 38.5 | None |

As seen from above, the resist composition using the resin having a side chain containing dithiane of the present embodiment has sufficient sensitivity and resolution without leaving residual in the exposed area.

Example 4

-Production of Semiconductor Device-

Figure 1A:
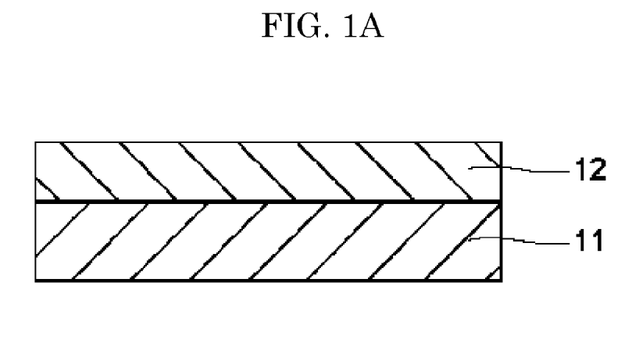
FIG. 1A is a schematic diagram explaining one example of a method for manufacturing a semiconductor device of the invention, and illustrates a state where an interlayer insulating film is formed on a silicon substrate.
Figure 1B:
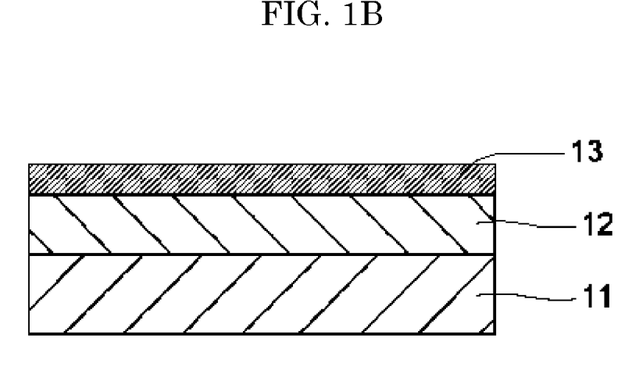
FIG. 1B is a schematic diagram explaining one example of a method for manufacturing a semiconductor device of the invention, and illustrates a state where a titanium film is formed on the interlayer insulating film of FIG. 1A.
Figure 1C:
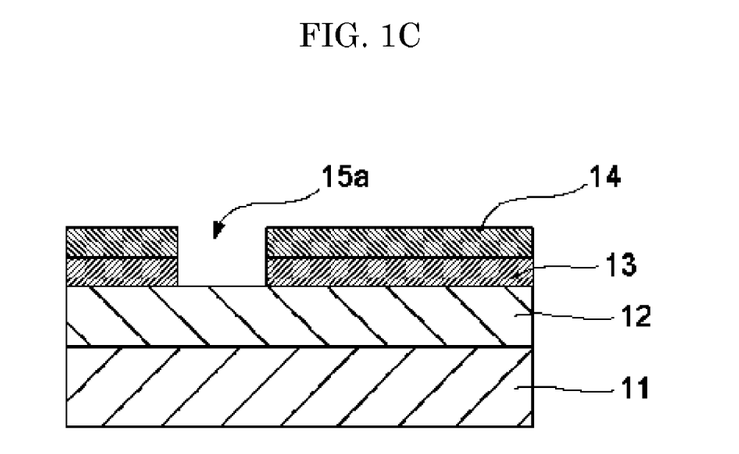
FIG. 1C is a schematic diagram explaining one example of a method for manufacturing a semiconductor device of the invention, and illustrates a state where a resist film is formed on the titanium film, and a hole pattern is formed in the titanium film.
Figure 1D:
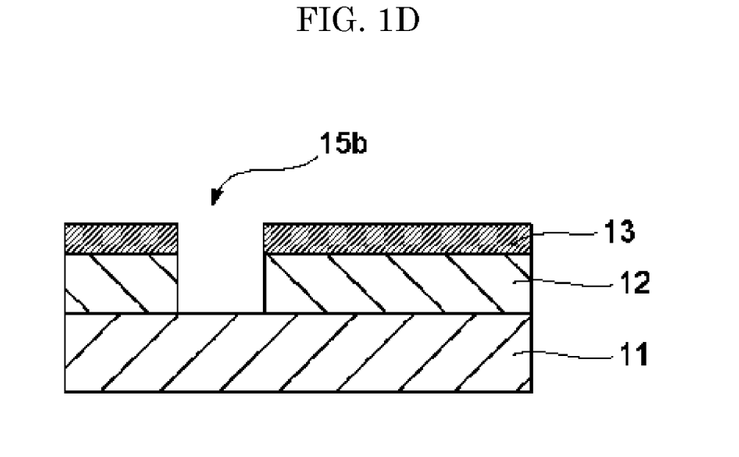
FIG. 1D is a schematic diagram explaining one example of a method for manufacturing a semiconductor device of the invention, and illustrates a state where the hole pattern is also formed in the interlayer insulating film.

An interlayer insulating film 12 was formed on a silicon substrate 11 as illustrated in FIG. 1A, and a titanium film 13 was formed on the interlayer insulating film 12 in accordance with a sputtering method as illustrated in FIG. 1B. Sequentially, a resist pattern 14 was formed by an ArF liquid immersion exposure as illustrated in FIG. 1C, and using the resist pattern 14 as a mask, the titanium film 13 was subjected to patterning by reactive ion etching so as to form an opening 15a. The reactive ion etching was continuously preformed so as to remove the resist pattern 14, as well as forming an opening 15b in the interlayer insulating film 12 using the titanium film 13 as a mask as illustrated in FIG. 1D.

Figure 1E:
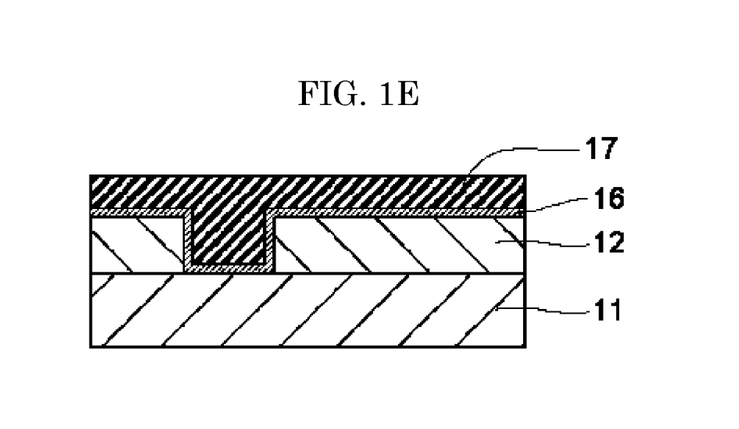
FIG. 1E is a schematic diagram explaining one example of a method for manufacturing a semiconductor device of the invention, and illustrates a state where a Cu film is formed on the interlayer insulating film to which the hole pattern has been formed.
Figure 1F:
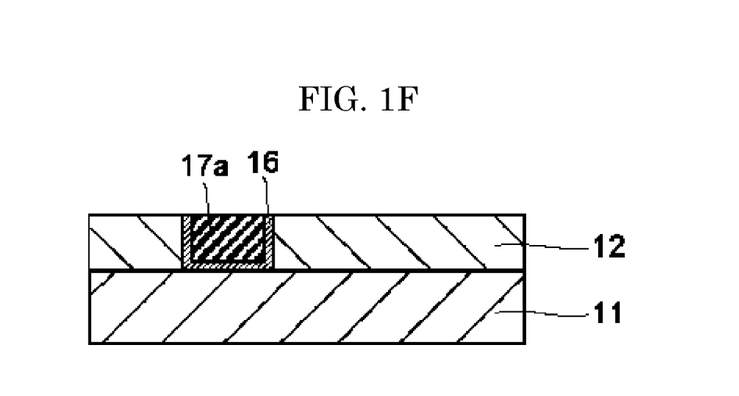
FIG. 1F is a schematic diagram explaining one example of a method for manufacturing a semiconductor device of the invention, and illustrates a state where the Cu deposited on the interlayer insulating film other than on the hole pattern is removed.

Thereafter, the titanium film 13 was removed by a wet treatment, and a TiN film 16 was formed on the interlayer insulating film 12 in accordance with a sputtering method as illustrated in FIG. 1E and a Cu film 17 was sequentially formed on the TiN film 16 in accordance with an electroplating method. As illustrated in FIG. 1F, the surface was smoothened by CMP while leaving only a barrier metal and the Cu film (first metal film) in a trench corresponding to the opening 15b (FIG. 1D) so as to form a wiring 17a of a first layer.

Figure 1G:
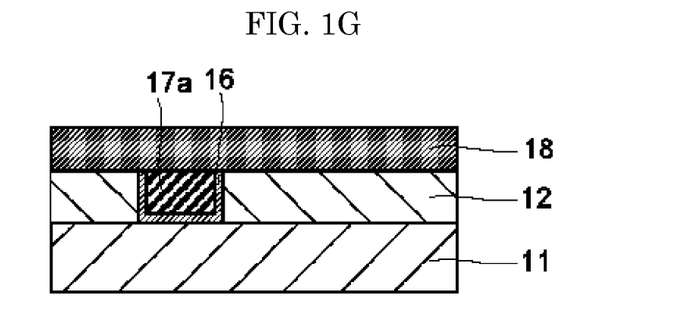
FIG. 1G is a schematic diagram explaining one example of a method for manufacturing a semiconductor device of the invention, and illustrates a state where an interlayer insulating film is formed on the Cu plug formed in the hole pattern and on the interlayer insulting film.
Figure 1H:
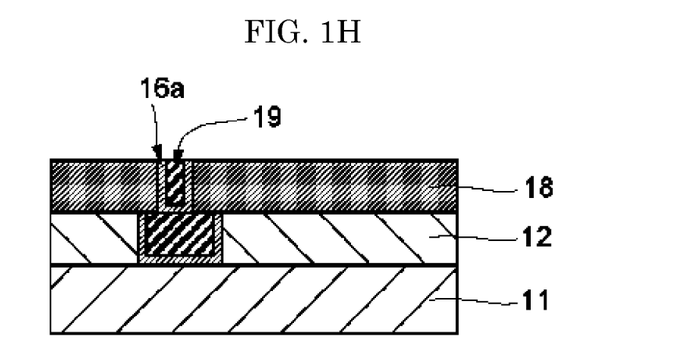
FIG. 1H is a schematic diagram explaining one example of a method for manufacturing a semiconductor device of the invention, and illustrates a state where a hole pattern is formed in the interlayer insulating layer as the surface layer, and a Cu plug is formed therein.

Thereafter, an interlayer insulating film 18 was formed on the wiring 17a of the first layer as illustrated in FIG. 1G, and then, as illustrated in FIG. 1H, onto the wiring 17a of the first layer, a Cu plug (second metal film) 19 and a TiN film 16a which would be connected with a wiring of an upper layer formed later were formed in the same manner as illustrated in FIGS. 1A to 1F.

Figure 1I:
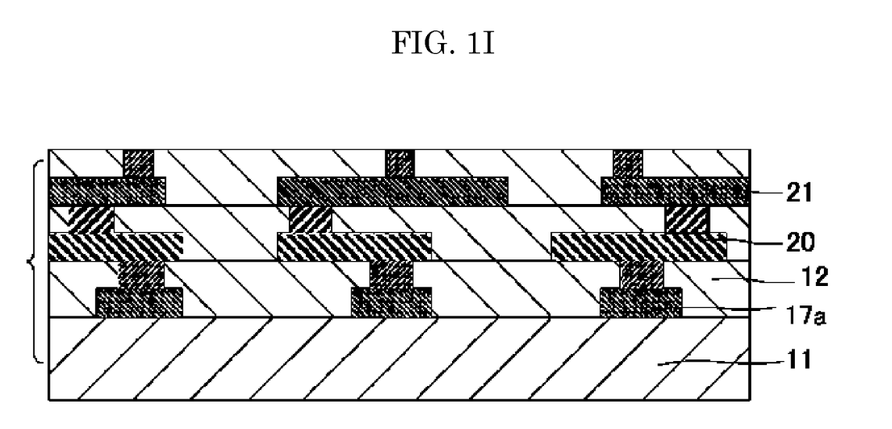
FIG. 1I is a schematic diagram explaining one example of a method for manufacturing a semiconductor device of the invention, and illustrates a state where a three-layered wiring is formed.

By repeating each aforementioned process, a semiconductor device having a multi-layered wiring structure containing the first layer wiring 17a, the second layer wiring 20 and the third layer wiring 21 disposed on the silicon substrate 11 was formed as illustrated in FIG. 1I. Note that, barrier metal layers each formed under each wiring were not illustrated in FIG. 1I.

In Example 4, the resist pattern 14 was a resist pattern formed by using the resist composition of Example 3. Moreover, the interlayer insulating film 12 was formed with a low dielectric constant material having a dielectric constant of 2.7 or less, e.g. a porous silica film (CERAMATE NCS, manufactured by JGC Catalysts and Chemicals Ltd., dielectric constant: 2.25), or a fluorocarbon film (dielectric constant: 2.4) accumulated in accordance with a RFCVD method (power: 400 W) using a mixed gas of $C_4F_8$ and $C_2H_2$ or $C_4F_8$ gas as a source.

According to the aspects of the invention described above, a finer and more accurate pattern can be formed by a high-refractive liquid immersion lithography using ArF excimer laser beams, which can draw finer patterns. Therefore, these aspects of the invention largely contribute to mass-production of devices.

In the examples above, the production methods of the dithiane derivative, or the polymer containing the monomer unit containing the dithiane derivative are described. However, these production methods are merely described as examples, and it should be noted that the dithiane derivative or the polymer can be also obtained in other conventional methods.

Moreover, the method for manufacturing a semiconductor can be applied to the productions of those having a fine pattern, e.g., a mask pattern, a reticle pattern, functional parts such as metal plugs, various wirings, magnetic heads, liquid crystal displays (LCD), plasma display panels (PDP), and a surface acoustic wave (SAW) filter, optical parts used for connection of optical wirings, and minute parts such as microactuator. In such productions, the same effects can be attained due to the same functions.

Moreover, in the example above, the production process of the flash memory was specifically explained as an example of the semiconductor, but the example thereof shall not be restricted to the flash memory. The method for manufacturing a semiconductor can also provide the same effect when it is applied to the production process of a logistic device, that of DRAM, or that of FRAM.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A polymer, comprising:
   a monomer unit containing a dithiane derivative, and
   a monomer unit containing an alicyclic group which is reactive to an acid,
   wherein the dithiane derivative has a structure expressed by the following general formula 1:

General Formula 1 where $R_1$ is —H, or —$CH_3$.

2. The polymer according to claim 1, further comprising a monomer unit containing a lactone group.

3. The polymer according to claim 1, wherein the alicyclic group is a 2-alkyladamanthyl group.

4. A resist composition, comprising:
   a polymer comprising a monomer unit containing a dithiane derivative and a monomer unit containing an alicyclic group which is reactive to an acid,
   wherein the dithiane derivative has a structure expressed by the following general formula 1:

General Formula 1 where $R_1$ is —H, or —$CH_3$.

5. The resist composition according to claim 4, wherein the resist composition has a refractive index of 1.530 or more with respect to light having a wavelength of 400 nm to 850 nm.

6. The resist composition according to claim 4, wherein the polymer is an acrylic resin.

7. The resist composition according to claim 4, further comprising an acid-generating agent.

8. The resist composition according to claim 4, further comprising a monomer of a dithiane derivative,
   wherein the dithiane derivative has a structure expressed by the following general formula 1:

General Formula 1 where $R_1$ is —H, or —$CH_3$.

9. The resist composition according to claim 4, wherein the polymer is a copolymer containing the monomer unit containing the dithiane derivative and one or more other monomer units, and wherein the resist composition further comprises a homopolymer of a dithiane derivative,
wherein the dithiane derivative has a structure expressed by the following general formula 1:

General Formula 1 where $R_1$ is —H, or —CH$_3$.

10. A method for manufacturing a semiconductor device, comprising:
forming a resist film on a processing surface using a resist composition;
selectively exposing the resist film to light; and
developing the resist film so as to pattern the resist film,
wherein the resist composition contains a polymer, and
wherein the polymer contains a monomer unit containing a dithiane derivative, in which the dithiane derivative has the structure expressed by the general formula 1:

General Formula 1 where $R_1$ is —H, or —CH$_3$.

11. The method according to claim 10, wherein the selectively exposing is selectively exposing the resist film to light in accordance with liquid immersion lithography, and a medium used for the liquid immersion lithography is either water or a liquid having higher refractive index than that of water with respect to light having a wavelength of 193 nm.

12. The method according to claim 10, further comprising etching the processing surface using the patterned resist film as a mask so as to pattern the processing surface.

13. The method according to claim 12, wherein the processing surface is a surface of a base, the base being formed of an insulating material having a dielectric constant of 2.7 or less.

* * * * *